United States Patent [19]

Lyons et al.

[11] Patent Number: 5,672,778
[45] Date of Patent: Sep. 30, 1997

[54] PROCESS FOR INCREASED YIELDS OF OXYGENATED PRODUCTS IN TWO-STEP OXIDATION OF HYDROCARBONS

[75] Inventors: James E. Lyons, Wallingford; Paul E. Ellis, Jr., Downingtown; Manoj V. Bhinde, Boothwyn, all of Pa.

[73] Assignee: Sun Company, Inc. (R & M), Philadelphia, Pa.

[21] Appl. No.: 703,423

[22] Filed: Aug. 26, 1996

Related U.S. Application Data

[63] Continuation-in-part of Ser. No. 398,024, Mar. 3, 1995, Pat. No. 5,550,301, which is a continuation-in-part of Ser. No. 223,090, Apr. 4, 1994, Pat. No. 5,395,988.

[51] Int. Cl.$^6$ ............ C07C 29/48; C07C 31/02; C07C 27/10
[52] U.S. Cl. ............ 568/835; 568/909.8; 568/815
[58] Field of Search ............ 568/835, 909.8, 568/815

[56] References Cited

U.S. PATENT DOCUMENTS

| | | |
|---|---|---|
| 3,879,467 | 4/1975 | Zajacek. |
| 5,004,837 | 4/1991 | Baur ............ 568/342 |

*Primary Examiner*—Jose G. Dees
*Assistant Examiner*—Jean F. Vollano
*Attorney, Agent, or Firm*—Q. Todd Dickinson; Stephen T. Falk

[57] ABSTRACT

The invention comprises a method for the catalytic conversion of alkanes and alkylhydroperoxides to oxygenates, particularly alcohols, comprising the oxidation of alkanes to yield alkylhydroperoxides, alcohols, other reaction products and unreacted alkane, and the decomposition of said alkylhydroperoxides to form alcohols and oxygen. Decomposition of the alkylhydroperoxide in the presence of unreacted alkane increases the yield of alcohol. The process further comprises drying of the reaction mixture comprising alkylhydroperoxide. Suitable catalysts for the process of the invention comprise metal containing catalysts, including metal organic ligand catalysts such as unsubstituted and substituted metal complexes of porphyrins, phthalocyanines and acetylacetonates.

57 Claims, No Drawings

PROCESS FOR INCREASED YIELDS OF OXYGENATED PRODUCTS IN TWO-STEP OXIDATION OF HYDROCARBONS

This application is a continuation-in-part of application Ser. No. 08/398,024, filed Mar. 3, 1995, now U.S. Pat. No. 5,550,301, which is a continuation-in-part of application Ser. No. 08/223,090, filed Apr. 4, 1994, now, U.S. Pat. No. 5,395,988.

FIELD OF THE INVENTION

The present invention pertains to the catalytic conversion of alkanes to oxygenates, particularly alcohols, comprising oxidation of the alkane feedstock to alkylhydroperoxides, alcohols and other oxygenates, and decomposition of said alkylhydroperoxides in the presence of alkane to form alcohols and other products.

BACKGROUND OF THE INVENTION

Processes for the catalytic oxidation of alkanes and the decomposition of alkylhydroperoxides are well known. See, for example, Brunie et at., U.S. Pat. No. 3,927,105, issued Dec. 16, 1975; Sanderson et at., U.S. Pat. No. 4,912,266, issued Mar. 27, 1990; Bhinde et al., U.S. Pat. No. 5,395,988, issued Mar. 7, 1995; and Sarneski et at., Alkyl Hydroperoxide Oxidation of Alkanes and Alkenes with a Highly Active Mn Catalyst, *Tetra. Lett.*, 32, 1153–1156 (1991); and the references cited therein.

Brunie et al., supra, disclose a process for the preparation of a mixture of cycloalkanones and cycloalkanols from hydroperoxides. They teach a process for oxidation of cycloalkane to a cycloalkyl hydroperoxide containing product, and decomposition of the hydroperoxide to a mixture of cycloalkanone and cycloalkanol, rich in cycloalkanone. The decomposition reaction is catalyzed by chromium compound soluble in the cycloalkane starting material.

Sarneski et al., supra, teach oxidation of alkanes, alkenes and alkylated arenes in the presence of alkyl hydroperoxide, such as TBHP, catalyzed by [$Mn_3O_4(2,2'$-dipyridyl$)_4(OH_2)_2$]($ClO_4)_4$.

Bhinde et al., U.S. Pat. No. 5,395,988, teaches decomposition of organic hydroperoxides catalyzed by metal organic ligand catalyst where the hydroperoxide feed or the reaction solvent, or both, are dried prior to the decomposition reaction.

An object of the present invention is to provide an efficient and economical means for the conversion of organic hydroperoxides to alcohols. A further object of the invention is to enable use of readily available catalyst compositions to catalyze the desired high-yield production of alcohols.

BRIEF DESCRIPTION OF THE INVENTION

The present invention comprises a method for converting alkanes to alcohols through the production of organic hydroperoxides and their subsequent decomposition in the presence of alkane. The invention may comprise the steps of oxidizing a feedstock comprising alkanes in a first step to form a first reaction mixture of oxidation products, comprising alkylhydroperoxides and unreacted alkanes, drying the first reaction mixture, thereby to obtain a dried reaction mixture such that water comprises approximately 1 weight percent or less of the dried reaction mixture, selectively decomposing a first portion of the alkylhydroperoxides in a second step in the presence of a catalyst to form a reaction mixture comprising oxygen and a mixture of oxygenated hydrocarbons comprising alcohols; decomposing a second portion of said alkylhydroperoxide and concomitantly oxidizing the unreacted alkanes in the presence of said catalyst to produce additional oxidation products comprising alcohols. Preferably, the production of alcohols and oxygenates is greater than 1 as a ratio of alcohol/oxygenate product to reacted alkylhydroperoxide, i.e., alkylhydroperoxide in said first reaction mixture which is converted during the process of the invention.

DETAILED DESCRIPTION OF THE INVENTION

The present invention comprises a method for converting alkanes to alcohols and other oxygenates through the production of organic hydroperoxides and their decomposition in the presence of alkane. In one embodiment, the invention comprises the steps of oxidizing a feedstock comprising alkanes in a first step to form a first reaction mixture of oxidation products, comprising alkylhydroperoxides and unreacted alkanes, drying the first reaction mixture, thereby to obtain a dried reaction mixture such that water comprises approximately 1 weight percent or less of the dried reaction mixture, selectively decomposing a first portion of the alkylhydroperoxides in a second step in the presence of a catalyst to form a reaction mixture comprising oxygen and a mixture of oxygenated hydrocarbons comprising alcohols; decomposing a second portion of alkylhydroperoxide and concomitantly oxidizing unreacted alkanes in said second step in the presence of said catalyst to produce additional oxidation products comprising alcohols; whereby production of alcohols and oxygenates is greater than 1 as a ratio of alcohol/oxygenate product to reacted alkylhydroperoxide in said first reaction mixture. In another embodiment, the process of the invention may be applied directly to the selective decomposition of a hydroperoxide feedstock in the presence of alkane and catalyst.

The Reaction Process

The process of the invention involves the steps of oxidizing an alkane or alkane-containing feedstock, drying the reaction product of that oxidation step, and decomposing the hydroperoxide in the dried reaction product, in the presence of unreacted and/or additionally introduced alkane, to yield alcohol. The step involving decomposition of the hydroperoxide and oxidation of the alkane is carried out in the presence of a catalyst. The process of the invention results in yields of alcohol greater than 100% relative to the molar amount of reacted hydroperoxide in the dried reaction product.

In one embodiment of the invention, hydrocarbon feed, for example alkane or alkylaromatic, is introduced into a first reaction zone where it is contacted with oxidant, such as oxygen or air, under suitable conditions to yield oxidation products and unreacted hydrocarbon. This oxidation reaction may be carried out in the absence of catalyst, though use of a catalyst to promote such oxidation reaction is within the scope of the invention, provided the catalyst does not decompose the hydroperoxide being formed. When the hydrocarbon feed comprises alkane, the oxidation reaction in the first reaction zone is carried out at sufficient temperature and pressure to yield a mixture of the corresponding hydroperoxide, alcohol, other minor oxidation products and unreacted alkane. For example, if the alkane is isobutane, the yield will comprise a mixture of t-butylhydroperoxide, t-butyl alcohol and isobutane. Suitable reaction parameters for this steps are readily determinable by the practitioner in the art; for example, the temperature may be in the range from 25° C. to 250° C., preferably 70° C. to 180° C., and the pressure may be in the range from 15 psig to 1500 psig, preferably 30 psig to 750 psig.

The reaction product from the first reaction zone, comprising organic hydroperoxide and unreacted hydrocarbon, is passed to a second reaction zone. In one embodiment, the reaction product is dried in a dryer unit placed between the first and second reaction zones. In another embodiment, the reaction product is dried in situ in the second reaction zone by means of a drying agent in the second reaction zone, for example through use of a granular solid drying agent. Suitable means for carrying out the drying step are taught in co-pending application Ser. No. 08/398,024, filed Mar. 3, 1995; and in Bhinde et at. U.S. Pat. No. 5,395,988.

Regardless of the means employed, the drying step serves to remove water from the reaction mixture such that water comprises approximately 1 weight percent or less of the dried reaction mixture. Preferably, the final amount of water is 0.5 wt. % or less of the dried reaction mixture, more preferably 0.25 wt. % or less, still more preferably 0.1 wt. % or less. Though not intending to be bound by any theory, it is believed that the removal of water from the catalytic reaction zone increases catalytic activity because water may compete with desired reactor substrate, such as hydroperoxide, for contact with catalyst. Under this theory, to the extent that catalyst is contacting or bound to water in the system, it is not available to catalyze the desired reaction.

The dried reaction mixture, comprising organic hydroperoxide and alkane or alkylaromatic or combination thereof, is contacted with catalyst in a second reaction zone under conditions suitable for decomposition of the hydroperoxide. The catalysts useful in the process of the invention may comprise metal organic ligand compositions, such as metalloporphyrins, metallophthalocyanines and metal acetylacetates, or metal compounds, such as metal halides and metal cyanides. Catalysts useful in the process of the invention are described more fully infra. Suitable reaction parameters for this steps are readily determinable by the practitioner in the art; for example, the temperature may be in the range from 25° C. to 150° C., preferably 60° C. to 120° C., and the pressure may be less than 500 psig, preferably 15 psig to 100 psig. A first portion of organic hydroperoxide is catalytically decomposed in this step to form oxygenated hydrocarbons comprising alcohol. A second portion of organic hydroperoxide is decomposed with concomitant oxidation of alkane present in the dried reaction mixture to form additional oxygenated hydrocarbons. The oxygenated hydrocarbons may comprise alcohols, ketones, acids and other oxidates; preferably, alcohols are the predominant product.

The decomposition and oxidation reactions which occur in the second reaction zone produce alcohol and other oxygenate product in yields greater than 1 as a ratio of alcohol/oxygenate produced to reacted hydroperoxide in the reaction mixture. Though not intending to be bound by any particular theory, it is believed that the following occurs to produce the alcohol yields of the process of the present invention: A portion of hydroperoxide in the reaction mixture is selectively decomposed in the presence of catalyst to produce predominantly alcohol and oxygen, with concomitant production of minor amounts of other oxidation products such as ketones and acids. At the same time, a portion of hydroperoxide may react with alkane in the reaction mixture, effectively transferring oxygen to the alkane and producing 2 moles of alcohol per mole of hydroperoxide and mole of alkane.

The Feedstock

The process of the present invention comprises a means for producing alcohols and ketones from decomposition of organic hydroperoxides. In one embodiment of the invention, the process comprises catalytic decomposition of hydroperoxide feed in the presence of alkane. In another embodiment of the invention, the feed comprises a hydrocarbon feedstock, preferably rich in alkane. The alkane component of the feed is oxidized, non-catalytically or catalytically, to produce oxidation products comprising hydroperoxide. The hydroperoxide is catalytically decomposed in the presence of alkane, either unreacted alkane from the oxidation step or alkane added to the decomposition reaction zone, to produce predominantly alcohol.

Organic hydroperoxides for decomposition according to the invention include compounds having the formula ROOH where R is an organic radical, typically (i) a straight or branched chain alkyl group or cycloalkyl group containing 4 to 15 carbon atoms, or an alkylaryl (or aralkyl) group in which the alkyl chain contains 1 to 15 carbon atoms and the aryl group is as above described. Preferably, R is an alkyl or cycloalkyl group containing 4 to 12 carbon atoms or an alkylaryl group in which the aromatic moiety is phenyl and the alkyl group is straight or branched chain alkyl or cycloalkyl containing up to 6 carbon atoms. More preferably, R is a secondary or tertiary alkyl, cycloalkyl, or alkylaryl group containing 3 or more carbon atoms.

Examples of hydroperoxides for decomposition according to the invention are t-butyl hydroperoxide, isoamyl hydroperoxide, t-amylhydroperoxide, cyclopentyl hydroperoxide, cyclohexyl hydroperoxide, cycloheptyl hydroperoxide, cyclooctyl hydroperoxide, benzyl hydroperoxide, alpha- and beta-ethylbenzene hydroperoxide, cumyl hydroperoxide, phenethyl hydroperoxide and cyclohexylphenyl hydroperoxide; phenethyl hydroperoxide and cumyl hydroperoxide are converted to phenethyl alcohol and cumyl alcohol respectively. Preferred are the alkyl hydroperoxides such as t-butyl hydroperoxide, isoamyl hydroperoxide, and the like; the cycloalkyl hydroperoxides such as cyclohexyl hydroperoxide, methylcyclohexyl hydroperoxide, and the like; and the alkylaryl hydroperoxides, such as cumyl hydroperoxide, phenethyl hydroperoxide, and the like.

Where the process of the invention commences with oxidation of a hydrocarbon feed, the feed comprises compounds oxidizable to organic hydroperoxide, preferably alkanes, for example, isobutane, cyclopentane or cyclohexane, or alkylaromatics, for example, cumene or ethylbenzene. Generally, in this embodiment of the invention, the alkane present in the decomposition step is unreacted alkane from the oxidation step; in the case of an alkylaromatic feed, it is unreacted alkylaromatic from the oxidation step. However, alkane (or alkylaromatic) may be introduced to the decomposition step and this alkane (or alkylaromatic) may either be the same or different from the alkane (or alkylaromatic) present in the initial hydrocarbon feed. For example, where isobutane is initially oxidized to t-butyl hydroperoxide, the alkane present in the decomposition step may either be unreacted isobutane, or it may be isobutane or other alkane which is added to the reaction zone. The term "alkane" is generally used herein in describing the process of the invention, though it is understood that suitable alkanes or alkylaromatics may be used in the various embodiments of the invention.

The Catalyst

Decomposition catalysts for use according to the invention comprise metal containing catalysts, such as the transition metal salt complexes and the transition metal complexes of ligands such as phthalocyanines, porphyrins, porphenes, porphycenes, acetylacetonates, 1,3-bis (arylimino) isoindolines such as "BPI", Schiff bases such as salen, saleph and the like, halogenated mono-, bi-, tri- and tetra-dentate ligand systems such as propanates, buryrates, benzoates, naphthenates, stearates, bipyridines, terpyridines, phenanthrolines, dithiocarbamates, xanthates, salicylaldimines, cyclam, dioxycyclams, pyrazolyl borates and tetraazamacrocycles such as tetramethyltetraazadibenzocyclo-heptadecane.

Among the transition metals, particularly suitable metals for the catalysts useful in the present invention include titanium, vanadium, chromium, manganese, iron, cobalt, copper and ruthenium. Preferably, the transition metal comprises chromium, manganese, kon, cobalt and ruthenium.

In one embodiment, transition metal salts useful as catalysts in the present invention include, for example, metal cyanides, metal halides, metal hydroxides, metal azides and metal nitrides. Among the metal halides, soluble metal chlorides, such as cobalt chloride, for example, are useful catalysts according to the invention. The metal salt catalysts may be prepared by any suitable means known to those in the art.

In another embodiment of the invention, transition metal ligand complexes of the types listed above are used as catalysts. Preferred among these are the ligands having the hydrogen atoms of the molecule substantially completely replaced with electron-withdrawing atoms or groups such as halogen, nitro, cyano, halocarbyl, nitrocarbyl, cyanoearbyl and the like. In a further embodiment, the catalysts may comprise anions associated with the coordination metal of the transition metal ligand complex. Suitable anions include halide, azide, nitride, hydroxide and carbonyl groups. In another embodiment, the metal may be linked by a μ-oxo bridge to the metal coordinated to a second ligand. The catalysts useful in the process of the present invention may be produced by conventional methods known in the art. See, Bhinde et al., U.S. Pat. No. 5,395,988, which is incorporated by reference herein; and the references cited herein.

An advantage of the present invention is that inexpensive and readily available compositions, which previously were completely or essentially inactive as catalysts, exhibit enhanced activity when utilized in the present invention. Examples of such catalysts are unsubstituted metallophthalocyanines and the metal acetylacetonates, such as cobalt acetylacetonate (Co(acac)$_2$) and ruthenium acetylacetonate (Ru(acac)$_3$). Further examples include soluble metal halides, such as cobalt chloride.

In one embodiment of the invention, the catalyst is a mixture of metallo-phthalocyanine and metal acetylacetonate, for example, iron phthalocyanine (FePc) and Co(acac)$_2$. In another, the catalyst is a mixture of rutheninm acetylacetonate and cobalt acetylacetonate; the former appears to produce a higher overall conversion rate while the latter exhibits a shorter induction period and greater initial reaction rate. The weight ratio of Ru(acac)$_3$ to Co(acac)$_2$ may be from 0.01:1 to 100:1 (Ru:Co), preferably 0.1:1 to 10:1, more preferably 0.1:1 to 1:1. The relative proportion of Co(acac)$_2$ to Ru(acac)$_3$ may be modified to balance reaction rate, conversion rate and catalyst cost. Effecting the desired balance is within the ability of the skilled practitioner in the art.

EXAMPLES

The following examples illustrate the present invention:

Example 1

Table 1 shows a comparison between the production of alcohol from the decomposition of hydroperoxide carried out in the presence or absence of alkane. In runs 1–4, 121 mmoles of isobutane was dissolved in 25 ml of benzene containing 0.013 mmoles of catalyst. The catalysts, as indicated in Table 1, were ruthenium perfluorotetraphenylporphyrin carbonyl (Ru(TPFP)CO), oxochromium tetraphenylporhyrin (Cr(TPP)O), ruthenium tetraphenylporphyrin carbonyl (Ru(TPP)CO), oxochromium perfluorotetraphenylporhyrin (Cr(TPFP)O). TBHP, tert-butyl hydroperoxide, 10 mmoles, was added to the benzene/isobutane mixture and stirred at room temperature for the duration of the reaction time (21–22 hours). Final reaction mixtures were analyzed by standardized glpc. Runs 5–8 were performed in the same manner, but without the addition of isobutane to the starting materials.

As is apparent from the data in Table 1, the yield of t-butyl alcohol (TBA) from the decomposition of TBHP was 107% to 144% of the initial molar amount of TBHP when the reaction occurred in the presence of isobutane. In contrast, in the absence of isobutane, the yield of TBA was only 77% to 88% of the initial molar amount of TBHP.

Example 2

Table 2 illustrates the apparent oxygen transfer occurring during the process of the invention for the decomposition of TBHP in cumene to form TBA and cumenol. In these runs, 0.013 mmole catalyst was dissolved in 216 mmoles cumene. TBHP, 20 mmoles, was then added under nitrogen gas. The mixture was stirred under nitrogen for the times indicated in Table 2 and the final reaction mixtures were analyzed by glpc.

The data in Table 2 show that a mixture of TBA and cumenol were produced in these runs catalyzed by iron tetramethoxyphenylporphyrin chloride (Fe(TMPP)Cl), iron tetraphenylporphyrin chloride (Fe(TPP)Cl), manganese tetraphenylporphyrin chloride (Mn(TPP)Cl), and manganese octaethylporphyrin chloride (Fe(OEP)Cl).

The following examples show the activity of various metal complexes for selectively decomposing cyclohexyl hydroperoxide in dry cyclohexane.

Example 3

Dry cyclohexyl hydroperoxide (54%), 0.5 ml, was added to a stirred solution of cyclohexane, 2.6 ml, containing Fe(TPPF$_{20}$Cl$_8$)Cl, 1.2 mg. The reaction mixture was stirred for 5 hours at room temperature. Iodometric titration showed that over 99% of the hydroperoxide had reacted. Gas chromatography of the reaction mixture showed that the major product of reaction was cyclohexanol and the minor product was cyclohexanone formed in a 9/1 ratio. The combination of

TABLE 1

METALLOPORPHYRIN-CATALYZED TBHP DECOMPOSITION VS. OXYGEN TRANSFER TO ISOBUTANE[a]

| Catalyst | Starting Materials, mmoles | | RXN T,HR | PRODUCTS, mmoles | | | | Minimum TBA from $C_4H_{10}$[b] | Minimum Ratio B/A[b] |
|---|---|---|---|---|---|---|---|---|---|
| | $i\text{-}C_4H_{10}$ | TBHP | | TBA | Acetone | DTBP | TBHP | | |
| Ru(TPFP)CO | 121 | 10 | 22 | 10.7 | 0.2 | 0.5 | — | 0.7 | 0.08 |
| Cr(TPP)O | 121 | 10 | 22 | 13.5 | 0.2 | 0.6 | — | 3.5 | 0.54 |
| Ru(TPP)CO | 121 | 10 | 21 | 14.4 | 0.2 | 0.7 | — | 4.4 | 0.79 |
| Cr(TPFP)O | 121 | 10 | 21 | 14.0 | 0.2 | 0.7 | — | 4.0 | 0.67 |
| Ru(TPFP)CO | 0 | 10 | 21.5 | 7.7 | 0.1 | 0.5 | — | | |
| Cr(TPP)O | 0 | 10 | 21.5 | 8.4 | 0.3 | 0.5 | — | | |
| Ru(TPP)CO | 0 | 10 | 21.5 | 8.6 | 0.1 | 0.5 | — | | |
| Cr(TPFP)O | 0 | 10 | 21.5 | 8.8 | 0.15 | 0.5 | — | | |

[a]Isobutane, 121 mmoles was dissolved in 25 mls benzene containing 0.013 mmoles catalyst. tert-Butyl hydroperoxide, 10 mmoles was added and the mixture stirred at room temperature for the designated time. Reaction mixtures analyzed by standardized glpc.
[b]Does not take into account the acetone and DTBP formed from TBHP.

TABLE 2

METALLOPORPHYRIN - CATALYZED OXYGEN TRANSFER FROM TBHP TO CUMENE[a]

| Catalyst | Starting Materials, mmoles | | RXN T,HR | TBA | PRODUCTS, GC Area % | | |
|---|---|---|---|---|---|---|---|
| | Cumene | TBHP | | | TBHP | Cumenol | Acetophenone |
| Fe(TMPP)Cl | 216 | 20 | 5.0 | 3.09 | — | 3.72 | 0.39 |
| | | | 24 | 3.37 | | 3.71 | 0.52 |
| Fe(TPP)Cl | 216 | 20 | 3.7 | 3.14 | — | 2.59 | 0.46 |
| | | | 24 | 3.06 | | 3.74 | 0.33 |
| Mn(TPP)Cl | 216 | 20 | 6.0 | 0.48 | 2.10 | 0.18 | 0.10 |
| | | | 24 | 0.92 | 1.53 | 0.21 | 0.13 |
| Mn(OEP)Cl | 216 | 20 | 7.0 | 0.38 | 2.18 | 0.22 | 0.05 |
| | | | 24 | 0.86 | 1.47 | 0.23 | 0.13 |
| Fe(TPP)Cl | 216 | 20 | <0.1 | 3.20 | 0.02 | 2.69 | 0.32 |
| | | | 0.5 | 3.10 | — | 3.71 | 0.39 |
| | | | 1.1 | 3.21 | — | 3.73 | 0.39 |

[a]The catalyst, 0.013 mmoles, was dissolved in cumene and 20 mmole of tert-butylhydroperoxide (TBHP) was added under $N_2$. The mixture was stirred under $N_2$, then analyzed by glpc.

cyclohexanol and cyclohexanone formed was greater than the amount of cyclohexyl hydroperoxide used (determined by iodometric titration of starting material) on a molar basis.

Example 4

Dry cyclohexyl hydroperoxide (54%), 0.5 ml, was added to a stirred solution of cyclohexane, 2.6 ml, containing a mixture of ruthenium triacetylacetonate, 1.1 mg, and cobalt bisacetylacetonate, 1.0 mg. The reaction mixture was stirred for 5 hours at room temperature. Iodometric titration showed that over 97% of the hydroperoxide had reacted. Gas chromatography of the reaction mixture showed that the major product of reaction was cyclohexanol and the minor product was cyclohexanone formed in a 9.5/1 ratio.

Example 5

When a dry cyclohexane oxidate rich in cyclohexyl hydroperoxide, 5.0 ml, is added to a stirred solution of cyclohexane, 25 ml, containing a catalytic quantity of tetrakis(pentafluorophenyl)beta-octachloroporphyrinato chromium chloride, cyclohexanol and cyclohexanone are formed in a total molar quantity in excess of the cyclohexyl hydroperoxide added.

Example 6

When a dry cyclohexane oxidate rich in cyclohexyl hydroperoxide, 5.0 ml, is added to a stirred solution of cyclohexane, 25 ml, containing a catalytic quantity of tetrakis(pentafluorophenyl)porphyrinato chromium chloride, cyclohexanol and cyclohexanone are formed in a total molar quantity in excess of the cyclohexyl hydroperoxide added.

Example 7

When a catalytic quantity of phthalocyanotochromium azide is added to a dry cyclohexane oxidate rich in cyclohexyl hydroperoxide, cyclohexanol and cyclohexanone are formed in total molar excess over the cyclohexyl hydroperoxide in the original feed.

Example 8

When a catalytic quantity of phthalocyanotochromium chloride is added to a dry cyclohexane oxidate rich in cyclohexyl hydroperoxide, cyclohexanol and cyclohexanone are formed in total molar excess over the cyclohexyl hydroperoxide in the original feed.

Example 9

When a catalytic quantity of perfluorophthalocyanotochromium chloride is added to a dry cyclohexane oxidate rich cyclohexyl hydroperoxide, cyclohexanol and cyclohexanone are formed in total molar excess over the cyclohexyl hydroperoxide in the original feed.

Example 10

When a catalytic quantity of perfluoropthalocyanotochromium azide is added to a dry cyclohexane oxidate rich in cyclohexyl hydroperoxide, cyclohexanol and cyclohexanone are formed in total excess over the cyclohexyl hydroperoxide present in the original oxidate.

Example 11

When a catalytic quantity of tetrakis (pentafluorophenylporphryinato) manganese azide is added to a dry cyclohexane oxidate rich in cyclohexyl hydroperoxide, cyclohexanol and cyclohexanone are formed in total molar excess over the cyclohexyl hydroperoxide present in the original oxidate.

What is claimed is:

1. A method for converting alkanes and alkylaromatics to oxygenated hydrocarbons comprising the steps of:
   (a) oxidizing a feedstock comprising alkane or alkylaromatics, or a combination thereof, to form a first reaction mixture comprising organic hydroperoxide and unreacted feedstock;
   (b) drying said first reaction mixture to obtain a dried reaction mixture in which water comprises approximately 1 weight percent or less of said dried reaction mixture;
   (c) decomposing said organic hydroperoxide in the presence of a catalyst and said unreacted feedstock such that:
      (i) a first portion of said organic hydroperoxide is decomposed to form a second reaction mixture comprising oxygen and a mixture of oxygenated hydrocarbons comprising alcohol, and
      (ii) a second portion of said organic hydroperoxide is decomposed with concomitant oxidation of said unreacted feedstock to form additional oxygenated hydrocarbons comprising alcohol.

2. Method of claim 1 wherein production of said oxygenated hydrocarbons is greater than 1 as a ratio of oxygenated hydrocarbon product to organic hydroperoxide reacted.

3. Method of claim 2 wherein production of said alcohol is greater than 1 as a ratio of alcohol product to organic hydroperoxide reacted.

4. Method of claim 1 wherein said water comprises approximately 0.5 weight percent or less of said dried reaction mixture.

5. Method of claim 4 wherein said water comprises approximately 0.25 weight percent or less of said dried reaction mixture.

6. Method of claim 5 wherein said water comprises approximately 0.1 weight percent or less of said dried reaction mixture.

7. Method of claim 1 wherein said catalyst comprises metal containing catalyst.

8. Method of claim 7 wherein said catalyst comprises metal organic ligand catalyst.

9. Method of claim 8 wherein said metal organic ligand catalyst comprises ligand selected from the group consisting of phthalocyanines, other tetraazamacrocycles, porphyrins, porphenes, porphycenes, 1,3-bis(arylimino)-isoindolines, acetylacetonates, Schiff bases, halogenated mono-, bi-, tri- and tetradentate ligand systems, or combinations thereof.

10. Method of claim 9 wherein said metal is selected from the group consisting of chromium, manganese, iron, ruthenium, cobalt, titanium, vanadium and copper.

11. Method of claim 9 wherein said catalyst comprises metal acetylacetonate or mixtures thereof.

12. Method of claim 11 wherein said catalyst comprises cobalt acetylacetonate.

13. Method of claim 11 wherein said catalyst comprises ruthenium acetylacetonate.

14. Method of claim 11 wherein said catalyst comprises a mixture of ruthenium acetylacetonate and cobalt acetylacetonate.

15. Method of claim 9 wherein said catalyst comprises a metallophthalocyanine.

16. Method of claim 15 wherein hydrogen atoms of said phthalocyanine have been replaced with electron-withdrawing atoms or groups.

17. Method of claim 16 wherein said electron-withdrawing atoms or groups are selected from selected from the group consisting of halogen, cyano, nitro and halocarbyl.

18. Method of claim 17 wherein said catalyst comprises a metallohalophthalocyanine.

19. Method of claim 18 wherein said catalyst comprises a metalloperhalophthalocyanine.

20. Method of claim 9 wherein said catalyst comprises a mixture of metallophthalocyanine and metal acetylacetonate.

21. Method of claim 20 wherein said catalyst comprises a mixture of iron phthalocyanine and cobalt acetylacetonate.

22. Method of claim 9 wherein said catalyst comprises a metalloporphyrin.

23. Method of claim 22 wherein hydrogen atoms of said porphyrin have been replaced with electron-withdrawing atoms or groups.

24. Method of claim 23 wherein said electron-withdrawing atoms or groups are selected from selected from the group consisting of halogen, cyano, nitro and halocarbyl.

25. Method of claim 24 wherein said catalyst comprises a metallohaloporphyrin.

26. Method of claim 25 wherein said catalyst comprises a metalloperhaloporphyrin.

27. Method of claim 7 wherein said catalyst comprises one or more compositions selected from the group consisting of metal cyanides, metal halides, metal hydroxides, metal azides and metal nitrides.

28. Method of claim 27 wherein said metal comprises a transition metal.

29. Method of claim 28 wherein said metal is selected from the group consisting of titanium, vanadium, chromium, manganese, iron, ruthenium, cobalt and copper.

30. Method of claim 27 wherein said catalyst comprises soluble metal chloride.

31. Method of claim 27 wherein said catalyst comprises cobalt chloride.

32. Method of claim 1 wherein said alkanes comprise isobutane, cyclopentane, cyclohexane or combinations thereof.

33. Method of claim 1 wherein said alkylaromatics comprise cumene, ethylbenzene or combinations thereof.

34. Method of claim 1 wherein said organic hydroperoxide comprises secondary or tertiary hydroperoxides comprising three or more carbon atoms.

35. Method of claim 34 wherein said organic hydroperoxide comprises alkylhydroperoxide, alkylarylhydroperoxide or combinations thereof.

36. Method of claim 35 wherein said alkylhydroperoxide comprises t-butyl hydroperoxide, amyl hydroperoxide or cyclohexyl hydroperoxide.

37. Method of claim 36 wherein said organic hydroperoxide comprises t-butyl hydroperoxide.

38. Method of claim 34 wherein said alkylarylhydroperoxide comprises cumyl hydroperoxide or phenethyl hydroperoxide.

39. Method of claim 1 wherein said decomposing and said oxidizing of said second step occur at a temperature in the range from about 25° C. to about 150° C. and at a total pressure not greater than about 500 psig.

40. Method of claim 39 wherein said temperature is in the range from 60° C. to 120° C.

41. Method of claim 39 wherein said pressure is in the range from 15 to 100 psig.

42. Method of claim 1 wherein said feedstock is oxidized in a first reaction zone and said organic hydroperoxide is decomposed in a second reaction zone.

43. Method of claim 1 wherein said first reaction is dried in a dryer situate between said first reaction zone and said second reaction zone.

44. Method of claim 1 wherein said first reaction mixture is contacted with a granular solid drying agent to remove water from said first reaction mixture.

45. A method for converting organic hydroperoxides in a feed to the corresponding alcohol, said method comprising drying said feed comprising organic hydroperoxide, hydrocarbon selected from the group consisting of alkanes and alkylaromatics, and water, to obtain a dried feed such that water comprises approximately 1 weight percent or less of said feed, and contacting said dried feed with a catalyst under conditions to yield a production of alcohol greater than 1 as a ratio of alcohol product to reacted hydroperoxide.

46. Method of claim 45 wherein said organic hydroperoxide comprises secondary or tertiary hydroperoxide comprising three or more carbon atoms.

47. Method of claim 46 wherein said organic hydroperoxide comprises alkylhydroperoxide or alkylarylhydroperoxide.

48. Method of claim 47 wherein said alkylhydroperoxide comprises t-butyl hydroperoxide, amyl hydroperoxide or cyclohexyl hydroperoxide.

49. Method of claim 48 wherein said alkylhydroperoxide comprises t-butyl hydroperoxide.

50. Method of claim 47 wherein said alkylarylhydroperoxide comprises cumyl hydroperoxide.

51. Method of claim 45 wherein said water comprises approximately 0.5 weight percent or less of said dried reaction mixture.

52. Method of claim 51 wherein said water comprises approximately 0.25 weight percent or less of said dried reaction mixture.

53. Method of claim 52 wherein said water comprises approximately 0.1 weight percent or less of said dried reaction mixture.

54. A method for converting alkylhydroperoxide to alcohol comprising the steps of:

(a) drying a reaction mixture comprising alkylhydroperoxide, alkane and water, to obtain a dried reaction mixture in which water comprises approximately 1 weight percent or less of said dried reaction mixture;

(b) decomposing said alkylhydroperoxide in said dried reaction mixture in the presence of a catalyst and said alkane such that (i) a first portion of said alkylhydroperoxide is decomposed to form oxygen and oxygenated hydrocarbons comprising alcohol, and (ii) a second portion of said alkylhydroperoxide is decomposed with concomitant oxidation of said unreacted alkane to form additional oxygenated hydrocarbons comprising alcohol.

55. Method of claim 54 wherein production of alcohol is greater than 1 as a ratio of alcohol product to reacted alkylhydroperoxide.

56. Method of claim 55 wherein said reaction mixture is produced by oxidation of an alkane feed.

57. A method for converting a feedstock comprising alkane and alkylhydroperoxide to alcohol comprising the steps of:

(a) drying said feedstock to obtain a dried reaction mixture in which water comprises approximately 1 weight percent or less of said dried feedstock;

(b) decomposing said alkylhydroperoxide in the presence of a catalyst to form a reaction mixture comprising oxygen and a mixture of oxygenated hydrocarbons comprising alcohol; and (c) concomitantly converting said alkane in the presence of said catalyst and said alkylhydroperoxide to produce additional oxidation products comprising alcohol;

wherein production of alcohol is greater than 1 as a ratio of alcohol product to reacted alkylhydroperoxide.

* * * * *